(12) United States Patent
Dawson et al.

(10) Patent No.: US 6,362,160 B1
(45) Date of Patent: Mar. 26, 2002

(54) IMMUNOPHILIN-BINDING AGENTS PREVENT GLUTAMATE NEUROTOXICITY ASSOCIATED WITH VASCULAR STROKE AND NEURODEGENERATIVE DISEASES

(75) Inventors: Ted M. Dawson, Baltimore; Joseph P. Steiner, Hampstead; Valina L. Dawson, Baltimore; George R. Uhl, Towson; Solomon H. Snyder, Baltimore, all of MD (US)

(73) Assignee: The Johns Hopkins University School of Medicine, Baltimore, MD (US)

( * ) Notice: Subject to any disclaimer, the term of this patent is extended or adjusted under 35 U.S.C. 154(b) by 0 days.

(21) Appl. No.: 08/082,848

(22) Filed: Jun. 30, 1993

(51) Int. Cl.$^7$ .................. A61K 38/00; A61K 31/70; A61K 31/436

(52) U.S. Cl. .................. 514/2; 514/8; 514/12; 514/31; 514/27

(58) Field of Search .................. 514/12, 2, 8, 456, 514/458, 326, 560, 31

(56) References Cited

U.S. PATENT DOCUMENTS 5,283,257 A * 2/1994 Gregory et al. ............. 514/458

OTHER PUBLICATIONS

Liu, J. et al., *Cell*, 66: 807–815, 1991.*
Bram, R.J. et al., *Molecular and Cellular Biology*, 13(8): 4760–4769, 1993.*
Sharkey, J. et al., *Nature*, 371 (6495): 336–339, 1994.*
Ulas, J. et al., *J. of Neuroscience*, 14 (II Part I): 6317–6324, 1994.*
*The Merck Manual of Diagnosis & Therapy*, 16$^{th}$ Edition, Berkow et al. (Eds) Rahway, NJ, 1992.*
Mori et al. *J. of Vet Med. Science* 55(4): 581–586 (1993).*
Dawson, et al., "Nitric Oxide Synthase NMDA and the Immunosuppressant, FK–506, Modulate Phosphorylation, Functio and Neurotoxicity", Soc. Neurosc. 22nd Ann. Mtg., Anaheim, CA (1992), Abstract 18(1):321.2.
Kolata, "Brain Research Makes It Look Easy" *New York Times*, p. C1, May 25, 1993.
Dawson, et al., "Nitric Oxide Mediates Glutamate Neurotoxicity in Primary Cortical Cultures", *Proc. Natl. Acad. Sci. USA*, 88:6368–6371 (1991).
Bredt, et al., "Nitric Oxide Synthase Regulatory Sites", *J. Biol. Chem.* 267(16):10976–10981 (1992).
Liu, et al., "Inhibition of T Cell Signaling by Immunophilin–Ligand Complexes Correlates with Loss of Calcineurin Phosphatase Activity," *Biochem.*, 31:3896–3901 (1992).
Garthwaite, "Glutamte, Nitric Oxide and Cell–Cell Signalling in the Nervous System", *TINS* 14(2):60–67 (1991).
Moncada, et al., "Nitric Oxide: Physiology, Pathophysiology, and Pharmacology," *Pharmacological Reviews* 43(2):109–142 (1991).
Choi, "Bench to Bedside: The Glutamate Connection", *Science* 258:241–243 (1992).
Steiner, et al., "High Brain Densities of the Immunophilin FKBP Colocalized with Calcineurin", *Nature* 358:584–587 (1992).
Koh, et al., "Neurons Containing NADPH–Diaphorase Are Selectively Resistant to Quinolinate Toxicity," *Science* 234:73–76 (1986).
Swanson, et al., "Cyclosporin–Mediated Inhibition of Bovine Calcineurin by Cyclophilins A and B," *Proc. Natl. Acad. Sci. USA* 893741–3745 (1992).
Fruman, et al., "Calcineurin Phosphatase Activity in T Lymphocytes is Inhibiited by FK 506 and Cyclosporin A," *Proc. Natl. Acad. Sci. USA* 89: 3686–3690 (1992).
Meldrum, et al., "Excitatory Amino Acid Neurotoxicity and Neurodegenerative Disease," *TIPS 11*: 379–387 (1990).
Choi, "Glutamate Neurotoxicity and Diseases of the Nervous System," *Neuron 1*: 623–634 (1988).
Dawson, et al., "A Novel Neuronal Messenger Molecule in Brain: The Free Radical, Nitric Oxide," *Annals of Neurology* 32(3):297–311 (1992).
Liu, et al., "Calcineurin is a Common Target of Cyclophilin–Cyclosporin A and FKBP–FK506 Complexes," *Cell* 66:807–815 (1991).

* cited by examiner

Primary Examiner—Marianne P. Allen
(74) Attorney, Agent, or Firm—Banner & Witcoff, Ltd.

(57) ABSTRACT

Immunophilin-binding agents inhibit the phosphatase calcineurin, leading to the increased phosphorylation of certain brain proteins, including nitric oxide synthase. The increased levels of phosphorylation of nitric oxide synthase inhibits the enzymatic production of nitric oxide. Thus the neurotoxic effects of glutamate, which are ordinarily the result of vascular strokes and other neurodegenerative diseases, are minimized, because the neurotoxic effects are at least partially mediated by nitric oxide. Thus immunophilin-binding drugs can be used therapeutically in the treatment of vascular stroke and neurodegenerative disorders such as Alzheimer's disease and Huntington's disease.

18 Claims, 3 Drawing Sheets

NOS $^{32}P$

C    0.5    1    2    16

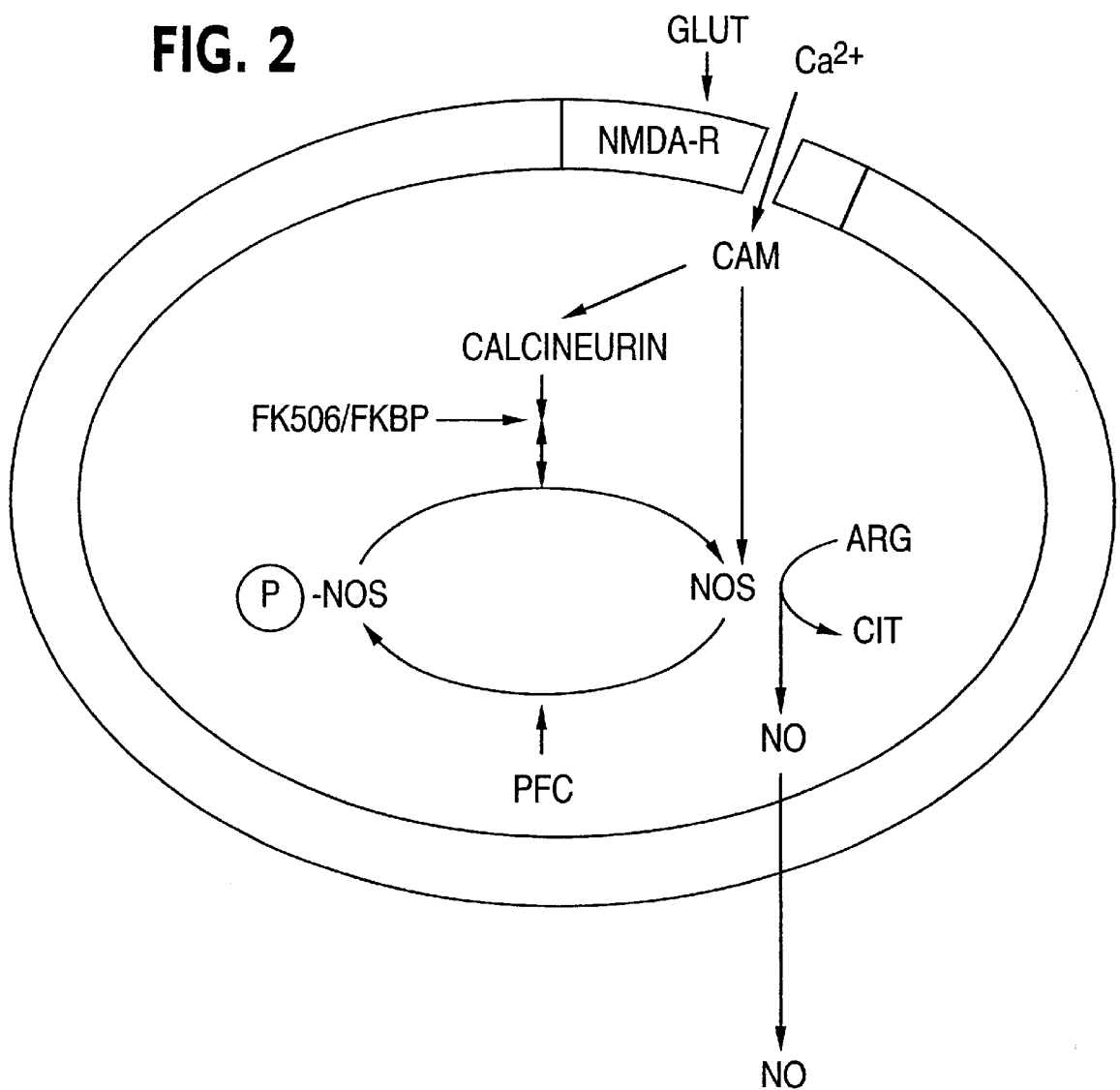

IMMUNOPHILIN-BINDING AGENTS PREVENT GLUTAMATE NEUROTOXICITY ASSOCIATED WITH VASCULAR STROKE AND NEURODEGENERATIVE DISEASES

The U.S. Government has a paid-up license in this invention and the right in limited circumstances to require the patent owner to license others on reasonable terms as provided for by the terms of grants awarded by the National Institutes of Health.

FIELD OF THE INVENTION

The invention relates to the use of inhibitors of calcineurin to prevent glutamate neurotoxicity.

BACKGROUND OF THE INVENTION

Nitric oxide (NO) has been demonstrated to mediate neuronal relaxation of intestines (Bult (1990) *Nature*, 345:346–347; Gillespie (1989) Br. *J. Pharmacol.*, 98:1080–1082; and Ramagopal (1989) *Eur. J. Pharmacol.*, 174:297–299) and to mediate stimulation by glutamate of cGMP formation (Bredt (1989) *Proc. Natl. Acad. Sci. USA* 86:9030–9033). Glutamate, the major excitatory neurotransmitter in the brain, acts through several receptor subtypes, some of which stimulate the formation of cGMP (Ferrendelli (1974) *J. Neurochen.* 22:535–540). Glutamate, acting at N-methyl-D-aspartate (NMDA) subtype of receptors, is responsible for neurotoxic damage in vascular strokes. Glutamate neurotoxicity has also been implicated in neurodegenerative disorders such as Alzheimer's and Huntington's diseases (Choi (1990) *J. Neurosci.* 10:2493–2501; and Meldrum (1990) *Trends in Pharmiacol. Sci.* 11:379–387). Selective antagonists of NMDA glutamate receptors prevent neuronal cell death in animal models of hypoxic-ischemic brain injury (Choi (1990) *J. Neurosci.*, 10:2493–2501). In addition, inhibitors of nitric oxide synthase prevent neuronal cell death (Dawson, *Proc. Natl. Acad. Sci., USA*, 88:6368 (1991)).

Besides their roles in the immune system, the immunophilins, cyclophilin and FK-506 binding protein (FKBP), are highly concentrated in the brain in discrete neuronal structures where they are co-localized with the $Ca^{+2}$ activated phosphatase, calcineurin (Steiner, et al., *Nature*, 358:584–587 (1992). Liu (*Cell*, 66:807–815 (1991)) demonstrated that very low concentrations of FK-506 and cyclosporin A, which bind to FKBP and cyclophilin, respectively, inhibit calcineurin, and Steiner showed that both drugs enhance the phosphorylation of a number of proteins in the brain. Glutamate neurotoxicity acting via N-methyl-D-aspartate (NMDA) receptors is implicated in neuronal damage associated with strokes and neurodegenerative diseases (Choi, *Neuron*, 1:623–634 (1988); Meldrum, et al., *Trends Pharmacol. Sci.*, 11:379–387 (1990); Choi, *Science*, 258:241–243 (1992)). In primary cerebral cortical cultures (Dawson, et al., *Proc. Natl. Acad. Sci., USA*, 88:6368–6371 (1991)), hippocampal slices (Izumi, et al., *Neurosci. Lett.*, 135:227–230 (1993)), and in animal models of focal ischemia Nowicki, et al., *Euro. J. Pharma.*, 204:339–340 (1991)), NMDA toxicity is mediated, at least in part, by nitric oxide (NO), as NO synthase (NOS) inhibitors block this toxicity.

Effective methods of preventing, treating or ameliorating diseases caused by glutamate neurotoxicity are needed in the art.

SUMMARY OF THE INVENTION

It is an object of the invention to provide a method of treating diseases caused by glutamate neurotoxicity.

It is another object of the invention to provide a method of treating vascular stroke and neurodegenerative diseases.

It is another object of the invention to provide a method of screening compounds to identify neuroprotective drugs.

These and other objects of the invention are provided by one or more of the embodiments described below. In one embodiment of the invention, a method for treating vascular stroke and neurodegenerative disease patients to block glutamate-mediated neurotoxicity is provided. The method comprises: administering to a vascular stroke or neurodegenerative disease patient a drug which binds to an immunophilin, in an amount effective to inhibit glutamate-mediated neurotoxicity.

In another embodiment of the invention, a method is provided for treating vascular stroke and neurodegenerative disease patients to block glutamate-mediated neurotoxicity. The method comprises: administering to a vascular stroke or neurodegenerative disease patient a drug which binds to an immunophilin, in an amount effective to inhibit calcineurin.

In still another embodiment of the invention, a method is provided for screening compounds to identify neuroprotective drugs. The method comprises the steps of: applying an immunophilin-binding test compound to cultured mammalian neuronal cells; applying a neurotoxic agent selected from the group consisting of NMDA and glutamate to said cultured mammalian neuronal cells; assessing toxicity by determining viability of the cultured mammalian neuronal cells, a neuroprotective drug being identified when a test compound inhibits the toxic effects of said neurotoxic agent.

Thus the present invention provides the art with methods for treating neurological diseases associated with glutamate neurotoxicity, as well as methods of identifying other pharmacological agents which will block glutamate neurotoxicity.

BRIEF DESCRIPTION OF THE DRAWINGS

FIG. 1 demonstrates that phosphorylation of nitric oxide synthase (NOS) is regulated by calcineurin and FK-506-FKBP. (FIG. 1D). The level of phosphorylation was determined quantitatively (FIG. 1E).

FIG. 2 proposes a mechanism for the regulation of the phosphorylation state and catalytic activity of NOS.

DETAILED DESCRIPTION OF THE INVENTION

Figure 1A:
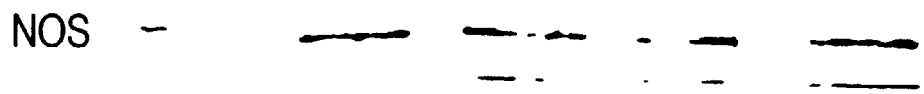
FIGS. 1A–1C show the dephosphorylation of phosphorylated purified brain NOS. $^{32}$P-labeled proteins were incubated with brain calcineurin for various times (FIG. 1B) and probed with anti-NOS antibody (FIG. 1A). The phosphorylation of NOS was quantitated and is shown in a bar graph (FIG. 1C).

It is a discovery of the present invention that immunosuppressant-type drugs, such as FK-506 and cyclosporin A, which bind to immunophilins, block glutamate neurotoxicity that is mediated by N-methyl-D-aspartate (NMDA) receptors. Upon binding of FK-506 and cyclosporin A to their respective immunophilins (binding proteins), the activity of the calcium-activated phosphatase calcineurin is inhibited. Thus treatment with this class of drugs increases the phosphorylation of proteins which are substrates of calcineurin. It is a further discovery of this invention that phosphorylated nitric oxide synthase (NOS) is a substrate for calcineurin. A model which accounts for these findings is that immunosuppressant-type drugs block neurotoxicity by inhibiting calcineurin, thereby increasing the phosphorylation of NOS, thereby inhibiting production of nitric oxide.

During the normal course of a vascular stroke or neurodegenerative disease, glutamate released from adjacent nerve terminals activates the NMDA subclass of glutamate receptors to increase intracellular $Ca^{2+}$ (Zorumski, et al., *Progr. Neurobiol.*, 39:295–336 (1992); Mayer, et al., *Ann. N.Y. Acad. Sci.*, 648:194–204 (1992)). The $Ca^{2+}$ binds to calmodulin, activating NOS. $Ca^{2+}$ entry also activates calcineurin, which dephosphorylates and activates NOS. The NO generated by NOS diffuses to adjacent cells to activate guanylate cyclase and increase intracellular cGMP levels (Moncada, et al., *Pharmacol. Rev.*, 43:109–142 (1991). If sufficient quantities of NO are produced, adjacent cells die (via undefined mechanisms) (Dawson, et al., *Ann. Neurol.*, 32:297–311 (1992)), whereas the neurons which produce NO are uniquely resistant. NOS catalytic activity is inhibited by protein kinase C (PKC)-mediated phosphorylation (Bredt, et al., *J. Biol. Chem.*, 267:10976–10981 (1992)).

FK-506, complexed to FKBP, binds to calcineurin, inhibiting its phosphatase activity. This prevents the dephosphorylation of NOS, which decreases NOS catalytic activity. With lowered NO production, adjacent neurons remain viable. Other immunophilin-binding drugs act by a similar mechanism.

The immunophilin-binding drugs may be used to prevent, treat, arrest, or ameliorate the progression of any disease condition caused by glutamate neurotoxicity. Such conditions include vascular strokes and neurodegenerative diseases, such as Alzheimer's, Huntington's and Parkinson's diseases, as well as other disease states. For example, following the symptoms of a stroke, an immunophilin-binding drug can be administered to a patient to block damage to the brain. Patients with symptoms of Alzheimer's or Huntington's disease can be treated with immunophilin-binding drugs to halt the progression of the disease. The symptoms of these disease states are known by one skilled in this art.

Immunophilin-binding drugs useful for the present invention are compounds which upon binding to immunophilins inhibit the activity of the phosphatase calcineurin and inhibit the toxicity of glutamate via NMDA-receptors. The present invention contemplates the use of any physiologically acceptable immunophilin-binding drug which inhibits calcineurin activity. The effectiveness of a compound, and its relative potency as a calcineurin inhibitor, can be tested and routinely determined by measuring inhibition of calcineurin activity, for example, by monitoring the level of phosphorylation of NOS in cerebellar homogenates or cultured neuronal cells. An increase in NOS phosphorylation indicates inhibitory activity of the compound. The magnitude of the increase in NOS phosphorylation, attributable to the presence of the compound being tested, indicates the potency of the compound as a calcineurin inhibitor. Alternatively, compounds can be tested to determine whether they inhibit the amount of NO formed, cGMP formed, or cell death occurring after treatment with glutamate or NMDA. The extent of inhibition of cGMP increases correlates with the ability to protect against neurotoxicity.

Both FK-506 and cyclosporin A, two immunophilin-binding calcineurin inhibitors, have been found to prevent neurotoxicity in proportion to their relative potencies as calcineurin inhibitors. In addition to these compounds, other immunophilin-binding drugs have been developed. Such drugs include FK-520, FK-523, 15-0-DeMe-FK-520, (4R)-[(E)-L-butenyl]-4,N-dimethyl-L-threonine. (Liu, *Biochemistry*, 31:3896–3902 (1992)).

The dosage and length of treatment with immunophilin-binding drugs depends on the disease state being treated. The duration of treatment may be a day, a week, or longer, and may, in the case of a chronic progressive illness, such as Alzheimer's disease, last for decades. The immunophilin-binding drugs are administered in a therapeutically effective amount, a typical human dosage of FK-506 ranging from about 0.1 mg/kg of body weight of FK-506 to about 1.0 mg/kg of FK-506, in single or divided doses. The dosage will vary depending on the immunophilin-binding drug to be used and its relative potency. Dosage and length of treatment are readily determinable by the skilled practitioner based on the condition and stage of disease.

In therapeutic use, immunophilin-binding drugs can be administered by any route whereby drugs are conventionally administered. Such routes of administration include intraperitoneally, intravenously, intramuscularly, subcutaneously, intrathecally and intraventricularly, as well as orally.

Typical preparations for administration include sterile aqueous or nonaqueous solutions, suspensions and emulsions. Examples of nonaqueous solvents are propylene glycol, polyethylene glycol, vegetable oils such as olive oil and injectable organic esters such as ethyl oleate. Aqueous carriers include water, alcoholic/aqueous solutions and buffered media. Intravenous vehicles include fluid and nutrient replenishers, electrolyte replenishers, such as those based on Ringer's dextrose, and the like. Preservatives and other additives may also be present such as, for example, antimicrobials, anti-oxidants, chelating agents, inert gases, and the like. Oral preparations, such as capsules, tablets, and other forms, can include additives such as cellulose, silica gel and stearic acid.

To be effective therapeutically, an immunophilin-binding drug desirably should be able to penetrate the blood-brain barrier when peripherally administrated. However, some immunophilin-binding drugs, like cyclosporin A, do not readily penetrate into the brain. Immunophilin-binding drugs which are unable to penetrate the blood-brain barrier can be effectively administered by, for example, an intraventricular route of delivery.

EXAMPLES

The following examples are provided to exemplify various aspects of the invention and are not intended to limit the scope of the invention.

Example 1

This example demonstrates that NOS is a substrate for calcineurin and that FK-506 enhances phosphorylation of NOS.

Purified brain NOS from NOS-transfected 293 kidney cells (Bredt, et al., *J. Biol. Chem.*, 267:10976–10981 (1992)), was preincubated with whole rat brain soluble fraction and phosphorylated by the endogenous protein kinase C in the whole rat brain soluble extracts (200 mg/ml net weight homogenate) plus 50 µg/ml phosphatidyl serine, 20 µM gramma $^{32}$P-ATP in 50 mM Hepes, 1 mm NaEGTA, 5 mm MgCl$_2$, 2mM DTT in pH 7.4 buffer for 20 min. at 25° C.

$^{32}$P-labeled proteins, transferred electrophoretically to nitrocellulose, were incubated with 5 nM brain calcineurin (Sigma, St. Louis, MO), 500 nM calmodulin, 10 µM free calcium, 20 µM MnCl$_2$ in 150 mM NaCl, 50 mM Hepes pH 7.5, 1 mM DTT, 0.5 mg/ml BSA buffer for various times at 25° C. Reactions were stopped by washing the nitrocellulose strips in ice cold buffer plus 2 mM NaEDTA three times, and autoradiograms were prepared. These same nitrocellulose strips were probed with affinity purified NOS antibody and developed with alkaline phosphatase-donkey anti-rabbit IgG. $^{32}$P-labeled NOS bands were excised at the various time points and compared with NOS immunoreactivity in these fractions. The level of phosphorylation of NOS was quantitated using the Eagle Eye Imaging System (Stratagene) and NIH Image (version 1.44) software (Sutherland, et al., *Biotech.*, 10:492–497 (1991), Correa-Rotter, et al., *Biotech.*, 12:154–158 (1992)).

Figure 1B:
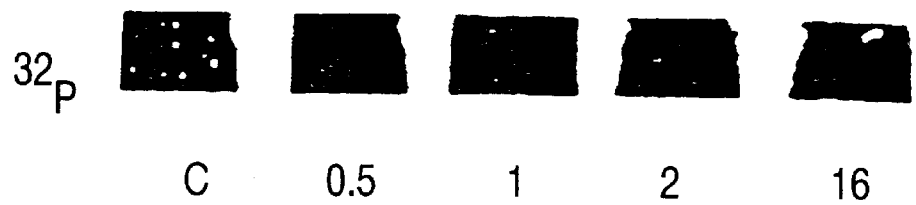
Figure 1C:
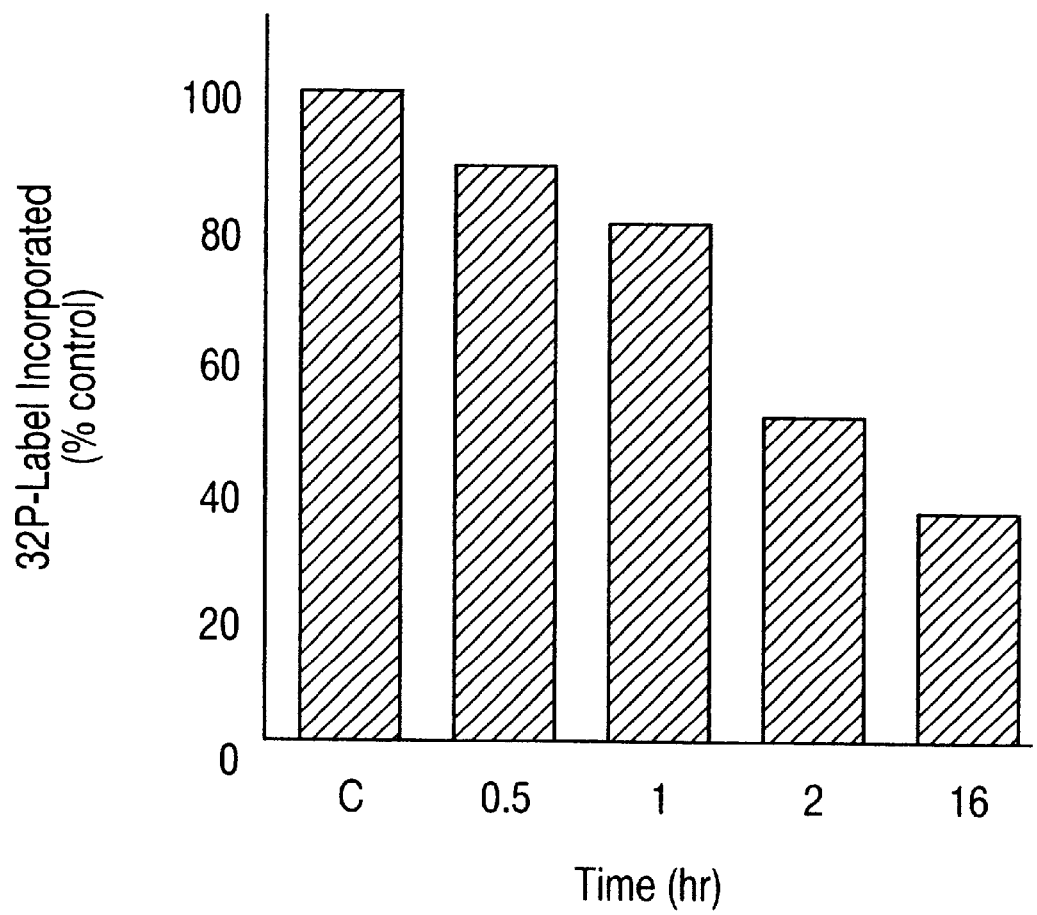

FIGS. 1A–1C show a representative dephosphorylation which has been replicated three times with similar results.

The data demonstrate that NOS is a calcineurin substrate by showing that NOS, phosphorylated following stimulation of protein kinase C activity with the phorbol ester O-tetradecanoylphorbol 13-acetate (TPA), is dephosphorylated in the presence of calcineurin.

Figure 1D:
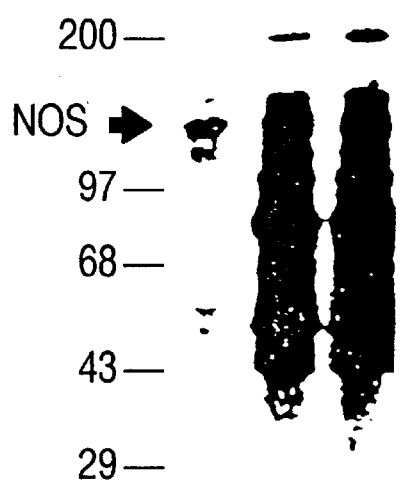
FIGS. 1D–E show that FK-506 enhances the phosphorylation of NOS. Purified brain NOS was labeled with $^{32}$p in the presence of 0-tetradecanoylphorbol 13-acetate (TPA) and whole rat brain soluble extracts. The proteins were resolved by polyacrylamide gel electrophoresis and autoradiographed.
Figure 1E:
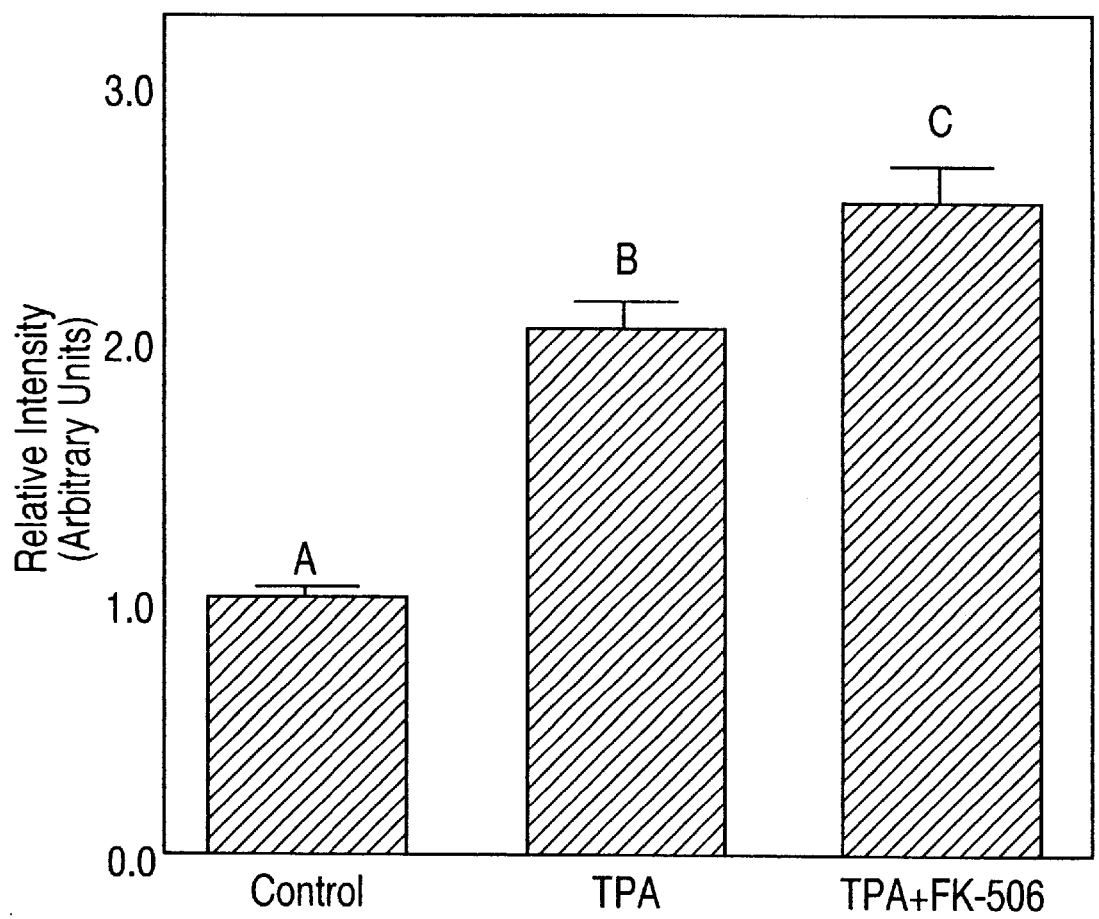

Purified brain NOS from NOS-transfected 293 kidney cells (Bredt, et al., *J. Biol. Chem.*, 267:10976–10981 (1992)), was then pre-incubated with whole rat brain soluble extracts (200 mg/ml wet weight homogenate) plus 50 µg/ml phosphatidylserine, 20 µM gamma $^{32}$P-ATP in 50 mM Hepes, 1 mM NaEGTA, 5 mM MgCl$_2$, 2 mM DTT in pH: 7.4 buffer in the absence or presence of 10 µM free Ca$^{2+}$, 200 nM TPA and 100 nM FK-506 for 20 min. at 25° C. Proteins were resolved on 3.5–17% linear gradient polyacrylamide gel using Laemmli buffers, gels were dried and exposed to X-ray film and autoradiograms were prepared. The results are as shown in FIG. 1D. (Lane A, control (no. Ca$^{2a+}$, no TPA), lane B, Ca$^{2+}$, TPA-stimulated phosphorylation, lane C, Ca$^{2+}$, TPA-stimulated phosphorylation in presence of 100 nM FK506.) Molecular weight markers, in kilodaltons, are indicated. The level of phosphorylation of purified NOS was quantitated as described above. This experiment has been replicated three times with similar results. The results demonstrate that TPA-stimulated phosphorylation of NOS is substantially increased in the presence of 100 nM FK-506 (see FIGS. 1D and 1E).

Example 2

This example demonstrates that FK-506 and cyclosporin A treatments markedly diminish NMDA neurotoxicity.

We monitored neurotoxicity in primary cerebral cortical neuronal cultures in which a 5 min. exposure to NMDA results in death of about 80% of neurons when observed 24 hrs. later (Dawson, et al., *Proc. Natl. Acad. Sci., USA*, 88:6368–6371 (1991)). Treatment of the cultures with FK-506 for 5 min. prior to application of NMDA and during the 5 min. of NMDA application provides marked protection from neurotoxicity (Table 1). As little as 25 nM FK-506 provides significant protection, while 50% protection is evident between 25–100 nM. To ascertain whether FK-506 exerts its protective effects by interacting with its receptor FKBP, we examined the effect of rapamycin which binds to FKBP and blocks effects of FK-506 (Liu, et al., *Cell*, 66:807–815 (1991); Chang, et al., *Trends Pharmacol. Sci.*, 12:218–223 (1991); Thomas, *Immunology Today*, 10:6–9 (1989); Schreiber, *Science*, 253:283–287 (1991)). Rapamycin (1 µM) completely reverses the effects of FK-506.

The immunosuppressants, FK-506 and cyclosporin A, exert a number of different actions but share the ability to inhibit the Ca$^{2+}$-dependent phosphatase activity of calcineurin (Liu, et al., *Cell*, 66:807–815 (1991); Fruman, et al., *Proc. Natl. Acad. Sci. USA*, 89:3686–3690 (1992); Swanson, et al., *Proc. Natl. Acad. Sci., USA*, 89:3741–3745 (1992); Liu, et al., *Biochemistry*, 31:3896–3901 (1992)). Cyclosporin A (1 µM) also protects against NMDA neurotoxicity, suggesting that the protection involves inhibition of calcineurin (Table 1). When applied by themselves, in the absence of NMDA, FK-506 (500 nM), cyclosporin (1 µM), and rapamycin (1 µM) have no effect on neuronal viability (data not shown). Moreover, FK-506 (500 nM) has no effect on NMDA elicited Ca$^{2+}$currents in these cultures (data not shown).

Earlier we showed that NMDA neurotoxicity in these cultures is prevented by inhibition of NO formation, suggesting that NO plays a role in NMDA neurotoxicity (Dawson, et al., *Proc. Nati. Acad. Sci., USA*, 88:6368–6371 (1991); Dawson, et al., *Ann. Neurol.*, 32:297–311 (1992)). While NMDA neurotoxicity involves NO, neurotoxicity following treatment with the glutamate derivatives quisqualate and kainate is not influenced by inhibition of NOS and so presumably involves other mechanisms such as oxygen free radicals (Choi, *Neuron*, 1:623–634 (1988); Meldrum, et al., *Trends Pharmacol. Sci.*, 11:379–387 (1990); Puttfarcken, et al., *Neuropharm.*, 31:565–575 (1992)). In our cultures quisqualate (500 µM) and kainate (100 µM) elicit as much cell death as glutamate (500 µM) (Table 1). However, whereas glutamate toxicity is inhibited by 500 nM FK-506 with this inhibition reversed by 1 µM rapamycin, 500 nM FK-506 fails to protect against quisqualate or kainate toxicity.

TABLE 1

FK-506 Attenuates NMDA Neurotoxicity

| Drug | % Cell Death (± S.E.M.) |
|---|---|
| 500 µM NMDA | 82.8 ± 4.3 |
| + 500 pM FK-506 | 78.3 ± 4.7 |
| + 1 nM FK-506 | 77.1 ± 4.0 |
| + 10 nM FK-506 | 68.5 ± 11.2 |
| + 25 nM FK-506 | *67.2 ± 4.1 |
| + 50 nM FK-506 | *61.9 ± 5.8 |
| + 100 nM FK-506 | *40.0 ± 9.1 |
| + 500 nM FK-506 | **29.7 ± 5.8 |
| + 1 µM FK-506 | **29.2 ± 4.1 |
| + 500 nM FK-506 + 1 µM RAPA | 82.4 ± 3.3 |
| + 1 µm CyA | *56.7 ± 4.8 |
| 500 µM Glutamate | 76.0 ± 5.2 |

TABLE 1-continued

FK-506 Attenuates NMDA Neurotoxicity

| Drug | % Cell Death (± S.E.M.) |
| --- | --- |
| + 500 nM FK-506 | *40.6 ± 3.9 |
| + 500 nM FK-506 + 1 μM RAPA | 61.7 ± 5.4 |
| 500 μM Quisqualate | 85.9 ± 6.0 |
| + 500 nM FK-506 | 90.5 ± 4.4 |
| 100 μM Kainate | 83.2 ± 6.3 |
| + 500 nM FK-506 | 88.1 ± 3.8 |

Statistical significance was determined by the Student's t-test
*p ≤ 0.05,
**p ≤ 0.0001.
Methods:
Primary neuronal cultures from cortex were prepared from fetal Sprague-Dawley rats gestation day 13–14. After dissection, the cells were dissociated by trituration, counted, and plated in 15 mm multi-well (Nunc) plates coated with polyornithine at a density of 3–4 x $10^5$ cells per well. Proliferation of non-neuronal cells was inhibited by applying 10 μg of 5-fluor-2'-deoxyuridine 4 days after plating for a total of 3 days. Neurons were maintained in modified Eagle's medium (MEM), 5% horse serum, 2 mM glutamine in 8% $CO_2$, humidified at 37° C. Media was changed twice a week. Mature neurons (greater than 21 days in culture) were used in all experiments. In these cultures neurons comprise approximately 70–90% of the total number of cells as assessed by neurons specific enolase and glial fibrillary acidic protein immunohistochemistry (unpublished observation). Neurotoxicity was determined by exposing the neurons to the various test solutions as previously described (Dawson, et al., Proc. Natl. Acad. Sci., USA, 88:6368–6371 (1991)). Prior to exposure, the cells were washed 3 times with a Tris-buffered control solution (CSS) containing 120 mM NaCl, 5.4 mM KCl, 1.8 mM $CaCl_2$, 25 mM Tris-HCl, 15 mM glucose at pH 7.4. FK-506 and cyclosporin A (CyA) were applied Statistical significance was determined by the Student's t-test *p ≤0.05, ** p≤0.0001.

Methods: Primary neuronal cultures from cortex were prepared from fetal Sprague-Dawley rats gestation day 13–14. After dissection, the cells were dissociated by trituration, counted, and plated in 15 mm multi-well (Nunc) plates coated with polyornithine at a density of 3–4×$10^5$ cells per well. Proliferation of non-neuronal cells was inhibited by applying 10 μg of 5-fluor-2'-deoxyuridine 4 days after plating for a total of 3 days. Neurons were maintained in modified Eagle's medium (MEM), 5% horse serum, 2 mM glutamine in 8% $CO_2$, humidified at 37° C. Media was changed twice a week. Mature neurons (greater than 21 days in culture) were used in all experiments. In these cultures neurons comprise approximately 70–90% of the total number of cells as assessed by neuron specific enolase and glial fibrillary acidic protein immunohistochemistry (unpublished observation).

Neurotoxicity was determined by exposing the neurons to the various test solutions as previously described (Dawson, et al., Proc. Natl. Acad. Sci., USA, 88:6368–6371 (1991)). Prior to exposure, the cells were washed 3 times with a Tris-buffered control solution (CSS) containing 120 mM NaCl, 5.4 mM KCl, 1.8 mM $CaCl_2$, 25 mM Tris-HCl, 15 mM glucose at pH 7.4. FK-506 and cyclosporin A (CyA) were applied 5 min. prior to and during the application of the excitatory amino acids. Rapamycin (RAPA) was applied 5 min. prior to and during the application of FK-506 and the excitatory amino acids. Following immunosuppressant drug pretreatment, NMDA and quisqualate were applied to the cells for 5 min., then the cells were washed with CSS and replaced with MEM, 21 mM glucose for 24 hr. in the incubator. Exposures to kainate were performed in MEM, 21 mM glucose for 24 hr. in the incubator. NMDA, quisqualate, and kainate were also applied to the neurons without immunosuppressant drug pretreatment. The effect of N-Arg (L-nitroarginine) on NMDA neurotoxicity was assessed as described (Dawson, et al., Proc. Natl. Acad. Sci., USA, 88:6368–6371 (1991)). Twenty to 24 hr. after exposure to test solutions, the neurons were exposed to 0.4% trypan blue in CSS to stain the residue of non-viable cells and to assess toxicity. Viable and non-viable cells were counted with approximately 500–1,500 cells counted per well. At least two separate experiments utilizing four separate wells were performed for each data point shown. A minimum of 4,000–12,000 neurons were counted for each data point. In some experiments photomicrographs were made before and after treatment using a transparent grid at the bottom of each culture plate. Viable and non-viable neurons in identical fields were counted by an observer blinded to study design and treatment protocol.

Example 3

This example demonstrates that the enhanced phosphorylation of NOS by F-506 diminishes functional NO activity.

We monitored cGMP levels in neuronal cultures (Table 2). In brain slices (Bredt, et al., Proc. Natl. Acad. Sci., USA, 86:9030–9033 (1989); Moncada, et al., Pharmacol. Rev., 43:109–142 (1991); Garthwaite, Trends Neurol. Sci., 14:60–67 (1991) and neuronal cultures (Dawson, et al., Proc. Nati. Acad. Sci., USA, 88:6368–6371 (1991)) NMDA increases cGMP levels several fold and the increase is prevented by NOS inhibitors (Dawson, et al., Proc. Natl. Acad. Sci., USA, 88:6368–6371 (1991), Bredt, et al., Proc. Natl. Acad. Sci., USA, 86:9030–9033 (1989)). In these cultures FK-506 (100 nM) reduces the NMDA stimulation of cGMP levels by approximately 80%. Rapamycin (1 μM) also diminishes the NMDA stimulation of cGMP. Evidence that FK-506 is acting at the level of NOS rather than blocking the effects of generated NO on guanylyl cyclase comes from our experiments showing that the stimulation of cGMP levels by sodium nitroprusside (SNP), which generates NO, is not affected by FK-506.

TABLE 2

FK-506 Inhibits NO Stimulated cGMP Formation

| Drug | % Basal cGMP Level (± S.E.M.) |
| --- | --- |
| 500 μM NMDA | 552.6 ± 95.6 |
| + 100 nM FK-506 | *89.3 ± 25.4 |
| + 100 NM FK-506 ± 1 μM RAPA | 178.3 ± 40.6 |
| + 1 μm CyA | *221.1 ± 31.9 |
| 300 μM SNP | 625.2 ± 85.4 |
| + 100 nM FK-506 | 509.9 ± 63.4 |

Methods:
Primary neuronal cortical cultures were treated under identical conditions as those used for assessment of neurotoxicity except for the addition of 100 μM isobutylmethylxanthine (IBMX) to all wells to inhibit phosphodiesterases. Immediately after the 5 min. application of NMDA or SNP (sodium nitroprusside) with or without the various other drugs, the cells were quenched with 15% trichloroacetic acid. Following ether extraction, cGMP was assayed utilizing an Amersham $^{125}$I-assay kit according to the manufacturer's instructions. Data represent the mean (± S.E.M.) of 6–12 wells (2–3 different plating of cultures) in duplicate.
Statistical significance was determined by the Student's t-test,
*p ≤ 0.005.

Methods: Primary neuronal cortical cultures were treated under identical conditions as those used for assessment of neurotoxicity except for the addition of 100 μM isobutylmethylxanthine (IBMX) to all wells to inhibit phosphodiesterases. Immediately after the 5 min. application of NMDA or SNP (sodium nitroprusside) with or without the various other drugs, the cells were quenched with 15% trichloroacetic acid. Following ether extraction, cGMP was assayed utilizing an Amersham [125] I-assay kit according to the manufacturer's instructions. Data represent the mean (±S.E.M.) of 6–12 wells (2–3 different plating of cultures) in duplicate. Statistical significance was determined by the Student's t-test, *p≦0.005.

In total, these data establish that immunophilin-binding drugs, by inhibiting calcineurin, cause the enhanced phosphorylation of NOS, thereby leading to lowered nitric oxide production. Thus immunophilin-binding, calcineurin-inhibiting drugs may be used therapeutically to treat neurotoxicity mediated through NMDA-type glutamate receptors.

What is claimed is:

1. A method for inhibiting glutamate-mediated neurotoxicity mediated by N-methyl-D-aspartate (NMDA) receptors in vascular stroke and neurodegenerative disease patients, comprising:

administering to a vascular stroke or neurodegenerative disease patient a drug which upon binding to an immunophilin inhibits calcineurin, in an amount effective to inhibit glutamate-mediated neurotoxicity mediated by NMDA receptors.

2. The method of claim 1 wherein the immunophilin is FK-506 binding protein (FKBP).

3. The method of claim 2 wherein the drug is FK-506.

4. The method of claim 1 wherein the immunophilin is cyclophilin.

5. The method of claim 4 wherein the drug is cyclosporin A.

6. The method of claim 1 wherein the drug is administered intravenously, intraperitoneally, intramuscularly, orally or intraventricularly.

7. The method of claim 1 wherein the patient is a vascular stroke patient.

8. The method of claim 1 wherein the patient is a neurodegenerative disease patient.

9. The method of claim 8 wherein the neurodegenerative disease is selected from the group consisting of Huntington's Disease, Alzheimer's Disease, and Parkinson's Disease.

10. A method for inhibiting glutamate-mediated neurotoxicity mediated by N-methyl-D-aspartate (NMDA) receptors in vascular stroke and neurodegenerative disease patients, comprising:

administering to a vascular stroke or neurodegenerative disease patient a drug which upon binding to an immunophilin inhibits calcineurin, in an amount effective to inhibit calcineurin.

11. The method of claim 10 wherein the immunophilin is FK-506 binding protein (FKBP).

12. The method of claim 11 wherein the drug is FK-506.

13. The method of claim 10 wherein the immunophilin is cyclophilin.

14. The method of claim 13 wherein the drug is cyclosporin A.

15. The method of claim 10 wherein the drug is administered intravenously, intraperitoneally, intramuscularly, orally or intraventricularly.

16. The method of claim 10 wherein the patient is a vascular stroke patient.

17. The method of claim 10 wherein the patient is a neurodegenerative disease patient.

18. The method of claim 17 wherein the neurodegenerative disease is selected from the group consisting of Huntington's Disease, Alzheimer's Disease, and Parkinson's Disease.

* * * * *